United States Patent [19]

Sharpe

[11] 3,957,999
[45] May 18, 1976

[54] ANILINOBENZOTHIAZOLES AS ANTIDEPRESSANTS

[75] Inventor: Christopher James Sharpe, Harrow Weald, England

[73] Assignee: The Boots Company, Nottingham, England

[22] Filed: Sept. 18, 1974

[21] Appl. No.: 506,994

Related U.S. Application Data

[62] Division of Ser. No. 343,565, March 21, 1973, Pat. No. 3,897,443.

[52] U.S. Cl. ............................... 424/270; 260/305
[51] Int. Cl.$^2$ .................................. A61K 31/425
[58] Field of Search .................... 424/270; 260/305; 343/565

Primary Examiner—Stanley J. Friedman
Attorney, Agent, or Firm—DeLio and Montgomery

[57] ABSTRACT

New anilinobenzothiazoles are used for treating depression.

13 Claims, No Drawings

ANILINOBENZOTHIAZOLES AS ANTIDEPRESSANTS

This is a division, of application Ser. No. 343,565 filed Mar. 21, 1973, now U.S. Pat. No. 3,897,443.

This invention relates to new chemical compounds with pharmacological activity. More particularly, the invention relates to new anilinobenzothiazoles of the formula I

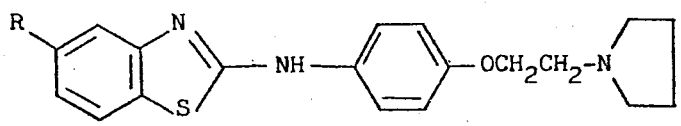

(I)

wherein R is hydrogen or methoxy, which possess antidepressant activity. Formula I encompasses two compounds, namely 5-methoxy-2-[4-(2-pyrrolidin-1-ylethoxy)anilino]benzothiazole and 2-[4-(2-pyrrolidin-1-ylethoxy)anilino]benzothiazole. These compounds are organic bases which form salts with inorganic and organic acids.

The compounds of formula I have properties consistent with their therapeutic value as antidepressants. Thus, when administered to warm-blooded animals in non-toxic doses by the oral or parenteral route, the compounds reverse reserpine-induced hypothermia, reverse reserpine-induced blepharoptosis, antagonise the sedative effect of tetrabenazine and inhibit the convulsant effect of leptazol.

In utilizing the therapeutic properties of the compounds of formula I, they may be administered as free bases or in the form of pharmaceutically acceptable acid addition salts thereof. Thus according to the present invention there are provided the new compounds of the hereinbefore defined formula I and pharmaceutically acceptable acid addition salts thereof. Such pharmaceutically acceptable acid addition salts may be formed with organic or inorganic acids and include, for example, the acetates, succinates, tartrates, citrates, hydrochlorides, hydrogen sulphates, and sulphates of the bases of formula I.

The compounds of the present invention may be administered orally, rectally or parenterally, preferably orally. In use, the compounds of the present invention are administered in conventional formulations and thus the present invention also provides therapeutic compositions which comprise as an active ingredient a compound of the hereinbefore defined formula I or a pharmaceutically acceptable acid addition salt thereof together with a pharmaceutically acceptable carrier. Pharmaceutically acceptable carriers suitable for use in the preparation of compositions suitable for oral, rectal or parenteral administration are well known in the art of pharmacy.

The compositions of the present invention suitably contain 0.1 – 90% by weight of active ingredient.

Compositions for oral administration are the preferred compositions of the invention, and these are the known pharmaceutical forms for such administration, for example, tablets, capsules, syrups and aqueous and oily suspensions. The excipients used in the preparation of these compositions are the excipients known in the pharmacist's art. Tablets may be prepared by mixing the active ingredient of the present invention with an inert diluent such as calcium phosphate in the presence of disintegrating agents, for example maize starch, and lubricating agents, for example magnesium stearate, and tableting the mixture by known methods. Such tablets may, if desired, be provided with enteric coatings by known methods, for example by the use of cellulose acetate phthalate. Similarly capsules, for example hard or soft gelatin capsules, containing a compound of the present invention with or without added excipients, may be prepared by conventional means and, if desired, provided with enteric coatings in a known manner. The tablets and capsules may conveniently each contain 10 – 500 mg. of a compound of the present invention. Other compositions for oral administration include, for example, aqueous suspensions containing a compound of the present invention in an aqueous medium in the presence of a nontoxic suspending agent such as sodium caboxymethylcellulose, and oily suspensions containing a compound of the present invention in a suitable vegetable oil, for example arachis oil.

Compositions of the invention suitable for rectal administration are the known pharmaceutical forms for such administration, for example suppositories with cocoa butter or polethylene glycol bases.

Compositions of the invention suitable for parenteral administration are the known pharmaceutical forms for such administration, for example sterile suspensions in aqueous and oil media or sterile solutions in a suitable solvent.

The compositions of the present invention may be made up in a dosage unit form suitable for the particular mode of administration to be used. For example, the dosage unit may exist in the form of a tablet, capsule or syrup suitable for oral administration, a suppository suitable for rectal administration, or a solution or suspension suitable for parenteral administration.

The present invention also provides a method of treating depression in warm-blooded animals, including man, which comprises the administration of a therapeutically effective dose of a compound of the hereinbefore defined formula I or a pharmaceutically acceptable acid addition salt thereof. A suitable dosage is generally within the range 0.05 – 50 mg./kg./day, more usually 0.1 – 25 mg./kg./day, and especially 0.5 – 15 mg./kg./day, given in single or divided doses.

The compounds of the present invention may be prepared by a process which comprises reacting pyrrolidine with a compound of the formula II

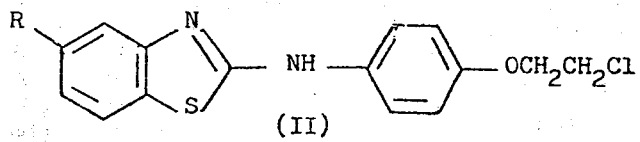

(II)

wherein R is hydrogen or methoxy.

The intermediate compounds of formula II may be prepared, for example, by reacting a 2-methylsulphonyl-5-R-benzothiazole with 4-(2-chloroethoxy)aniline. The reaction is suitably effected by heating the reactants together in a suitable inert organic solvent, for example toluene.

Another process for preparing the compounds of the present invention comprises reacting 4-(2-pyrrolidin-1-ylethoxy)phenyl isothiocyanate with a compound of the formula

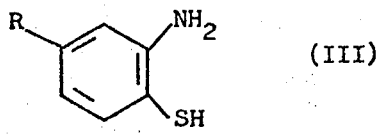

(III)

in which R is as hereinbefore defined. The reaction is suitably effected by heating the reactants in a suitable inert organic solvent, for example toluene.

The compounds of the present invention produced by the reactions described above may be isolated as free bases or as pharmaceutically acceptable acid addition salts thereof by means of conventional techniques. Similarly the free base compounds of the present invention may be converted to pharmaceutically acceptable acid addition salts thereof by reacting the appropriate base and acid together in a suitable organic solvent, for example ethanol, as the reaction medium.

A property possessed by antidepressants is that of reversing reserpine-induced hypothermia in standard laboratory animals such as mice. A test to evaluate this property was carried out with the compounds of formula I ($R = H$ or $CH_3O$). The test was carried out in mice as described by Shadbolt et al. in J. Med. Chem. vol. 14 p.837 (1971), and the following results were obtained.

| R | $ED_{50}$ (median effective dose) in mg./kg. |
|---|---|
| H | 3.7 |
| $CH_3O$ | 3.1 |

As shown by tests in standard laboratory animals, the compounds of formula I surprisingly possess superior pharmacological profiles as antidepressants in comparison with a variety of chemically related compounds, including 2-[4-(2-pyrrolidin-1-ylethoxy)anilino]benzoxazole (known from British Pat. Specification No. 1,153,647 as a compound with antidepressant properties), 2-[4-(2-diethylaminoethoxy)anilino]benzothiazole (known from British Patent Specification No. 1,034,538 as a compound with hypocholesterolaemic properties), and the anilinobenzothiazoles specifically exemplified in British Patent Specification No. 1,153,648. The latter specification is concerned with a group of anilinobenzothiazoles with antidepressant properties and there are claimed compounds of the general formula IV

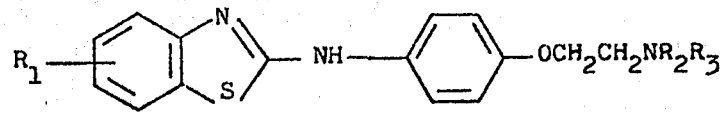

IV wherein $R_1$ represents hydrogen, halogen, lower alkyl containing up to 4 carbon atoms, trifluoromethyl, alkoxy or nitro and $R_2$ and $R_3$ are the same or different and represent hydrogen, lower alkyl containing up to 4 carbon atoms, β-hydroxyethyl or benzyl, except when $R_1$ is hydrogen and $R_2$ and $R_3$ are at the same time both lower alkyl; or $NR_2R_3$ represents a piperidino, morpholino or 4-methylpiperidino group.

The compounds of formula I possess a high level of activity (hereinafter referred to as antireserpine activity) in the hereinbefore mentioned reversal of reserpine-induced hypothermia test in mice, combined with a low level of undesirable side effects, and in this advantageous combination of properties the compounds of formula I exhibit the superior pharmacological profiles referred to above.

Thus the compound 2-[4-(2-pyrrolidin-1-ylethoxy)anilino]benzoxazole referred to above, which has a similar level of antireserpine activity to those of the compounds of formula I, has been shown to be markedly teratogenic in rats and rabbits, whereas comparative tests in animals at similar dosage levels with the compounds of formula I (rats for compound I, R=hydrogen; rats and rabbits for compound I, R=methoxy) gave no evidence of teratogenicity. Furthermore, the compounds of formula I have superior antireserpine activities to that of the compound 2-[4-(2-diethylaminoethoxy)anilino]benzothiazole referred to above. Also the latter compound possesses an undesirably high level of amphetamine-like CNS stimulant activity (as shown by the fact that in cats it produces amphetaminelike stereotyped reactions), in contrast to the compounds of formula which, in comparative tests at similar dosage levels, did not cause these stereotyped reactions. Another compound which, at similar dosage levels, causes amphetamine-like stereotyped reactions in cats is 2-[4-(2-piperidin-1-ylethoxy)anilino]benzothiazole, a compound which is specifically exemplified in British Patent Specification No. 1,153,648. This compound has a similar antireserpine activity to those of the compounds of formula I. The remaining compounds specifically exemplified in British Patent Specificiation No. 1,153,648 have inferior antireserpine activities to those of the compounds of formula I.

The following non-limitative examples illustrate the invention.

EXAMPLE 1

A. 4-(2-Chloroethoxy)aniline

A solution of 4-(2-hydroxyethoxy)acetanilide (1,084 g.), chloroform (2.08 liters) and dimethylformamide (144 ml.) is stirred and cooled with ice water during addition of a solution of thionyl chloride (475 ml.) in chloroform (720 ml.) during 45 minutes. The solution is then boiled under reflux for about 2.5 hours, one to two liters of chloroform distilled off at atmospheric pressure and most of the remainder at reduced pressure. The residue is treated with water (5.6 liters) and heated to remove residual chloroform. Concentrated hydrochloric acid (5.42 liters) is then added and the mixture boiled under reflux for one hour. The hot solution is filtered and the hydrochloride collected from the cooled filtrate. A solution of the hydrochloride in water (7.5 liters) at 60°C. is stirred and treated gradually with ammonia solution (density = 0.88, 350 ml.) to precipitate the product which is filtered off from the cooled mixture, washed with water and dried to give 4-(2-chloroethoxy)aniline, m.p. 91° – 92°C.

B. 5-Methoxy-2-[4-(2-chloroethoxy)anilino]benzothiazole

A mixture of 5-methoxy-2-methylsulphonylbenzothiazole (1,105 g.), 4-(2-chloroethoxy)aniline (780 g.) and toluene (5 liters) is boiled for 2 hours under reflux with simultaneous removal of water. A further quantity of 4-(2-chloroethoxy)aniline (156 g.) is then added and the mixture boiled under reflux for 4 hours. The mixture is cooled, the solid filtered off, washed with ethanol (about 3 liters) and dried to give 5-methoxy-2-[4-(2-chloroethoxy)anilino]benzothiazole m.p. 176°–178°C.

C. 5-Methoxy-2-[4-(2-pyrrolidin-1-ylethoxy)-anilino]benzothiazole

A mixture of 5-methoxy-2-[4-(2-chloroethoxy)anilino]benzothiazole (200 g.), pyrrolidine (144 ml.) and 2-methoxyethanol (1 liter) is boiled under reflux for 16 hours. The mixture is evaporated from the steam bath at reduced pressure and the residue dissolved in approximately 2N hydrochloric acid. The solution is washed with ethyl acetate, basified with 40% sodium hydroxide solution and extracted with chloroform. The chloroform is washed with water, dried over magnesium sulphate and passed through a column of alumina. The column is washed with chloroform and the combined chloroform solutions evaporated. The residue is recrystallised from 2-methoxyethanol to give 5-methoxy-2-[4-(2-pyrrolidin-1-ylethoxy)anilino]benzothiazole, m.p. 167° – 168°C.

In a analogous manner to that described above there are prepared 2-[4-(2-pyrrolidin-1-ylethoxy)anilino]-benzothiazole, m.p. 135.5° – 137°C. and the intermediate compound 2-[4-(2-chloroethoxy)anilino]benzothiazole, m.p. 173° – 174°C.

EXAMPLE 2

A. 4-(2-Pyrrolidin-1-ylethoxy)phenyl isothiocyanate 4-(2-Pyrrolidin-1-ylethoxy)aniline (17.3 g.) in ethanol (20 ml.) is added dropwise to a mixture of ethanol (55 ml.), carbon disulphide (10 ml.) and aqueous ammonia (density = 0.88, 20 ml.) at 0°C. After 2 hours the solid is collected and washed with acetone, m.p. 143° – 150°C. (dec.). This solid (23.6 g.), chloroform (114 ml.) and triethylamine (11.9 ml.) are stirred, and ethyl chloroformate (8.6 ml.) added with cooling so that the temperature remains below 0°C. After stirring for 30 minutes below 0°C. and 1 hour at 20°C., excess of 10% sodium hydroxide is added. The chloroform is separated, washed with water, dried and evaporated. The residue is dissolved in benzene and the solution filtered through alumina. The filtrate is evaporated and the residue distilled to give 4-(2-pyrrolidin-1-ylethoxy)-phenyl isothiocyanate, b.p. 160° – 168°C./0.2 mm.

The isothiocyanate forms a hydrochloride, m.p. 149° – 150°C. (from chloroform/petroleum ether b.p. 60° – 80°C.)

B. 5-Methoxy-2-[4-(2-pyrrolidin-1-ylethoxy)anilino]-benzothiazole

Triethylamine (0.7 ml.) is added to a suspension of 2-amino-4-methoxybenzenethiol hydrochloride (0.96 g.) in toluene (20 ml.) under nitrogen. 4-(2-Pyrrolidin-1-ylethoxy)phenyl isothiocyanate (1.24 g.) is added and the mixture stirred and heated under reflux for 16 hours. Ethyl acetate and 10% sodium hydroxide are added and the organic layer separated, washed with water and dried. The organic layer is passed through a column of silica gel (2 × 20 cm.) and the filtrate rejected. The column is eluted with methanol, which, on concentration gives 5-methoxy-2-[4-(2-pyrrolidin-1-ylethoxy)anilino]benzothiazole, m.p. 167° – 168°C.

In a similar manner there is prepared the compound 2-[4-(2-pyrrolidin-1-ylethoxy)anilino]benzothiazole, m.p. 135.5° – 137°C.

EXAMPLE 3

A. A solution of 5-methoxy-2-[4-(2-pyrrolidin-1-ylethoxy)anilino]benzothiazole (0.369 g.) in ethanol (14 ml.) is treated at room temperature with a solution of dry hydrogen chloride in ethanol (0.37 ml. of 10% w/v solution) and the mixture kept at room temperature for 24 hours. The precipitate which forms is collected by filtration, washed with dry ether and dried to give 5-methoxy-2-[4-(2-pyrrolidin-1-ylethoxy)anilino]benzothiazole hydrochloride hemihydrate, m.p. 196° – 199°C. with previous softening. Elemental analysis satisfactory for $C_{20}H_{24}ClN_3O_2S.\tfrac{1}{2}H_2O$.

B. A hot solution of 5-methoxy-2-[4-(2-pyrrolidin-1-ylethoxy)anilino]benzothiazole (0.738 g.) in ethanol (45 ml.) is treated with a hot solution of citric acid (0.384 g.) in ethanol (2.5 ml.). The solution is allowed to cool to room temperature and then kept at 0° – 10°C. overnight. The precipitate which forms is collected by filtration, washed with ethanol and dried to give 5-methoxy-2-[4-(2-pyrrolidin-1-ylethoxy)anilino]benzothiazole citrate, m.p. 155° – 156°C. (dec.) with previous softening. Elemental analysis satisfactory for $C_{26}H_{31}N_3O_9S$.

EXAMPLE 4

A solution of 5-methoxy-2-[4-(2-pyrrolidin-1-ylethoxy)anilino]benzothiazole (0.738 g.) in ethanol (30 ml.) is treated at room temperature with a solution of succinic acid (0.236 g.) in ethanol 3.5 ml.). After 1 hour the solution is diluted with ether (70 ml.) and then kept at 0° – 10°C. overnight. The resulting precipitate is collected by filtration and dried to give 5-methoxy-2-[4-(2-pyrrolidin-1-ylethoxy)anilino]benzothiazole succinate, m.p. 150° – 153°C. Elemental analysis satisfactory for $C_{24}H_{29}N_3O_6S$.

In a similar manner the following salts of 2-[4-(2-pyrrolidin-1-ylethoxy)anilino]benzothiazole are pepared:
A. Hydrochloride, m.p. 205° – 207°C. with previous softening. Elemental analysis satisfactory for $C_{19}H_{22}ClN_3OS$. B. Bis { 2-[4-(2-pyrrolidin-1-ylethoxy)anilino]benzothiazole} succinate, m.p. 186° – 187°C. Elemental analysis satisfactory for $C_{42}H_{48}N_6O_6S_2$.

EXAMPLE 5

In the preparation of tablets, the following mixture is dry granulated and compressed in a tableting machine to give tablets containing 25 mg. of active ingredient:

| | |
|---|---|
| 5-Methoxy-2-[4-(2-pyrrolidin-1-ylethoxy)anilino]benzothiazole | 10 g. |
| lactose | 5 g. |
| calcium phosphate | 5 g. |
| maize starch | 5 g. |

In a similar manner tablets are prepared containing 10 mg. of active ingredient.

EXAMPLE 6

In the preparation of enteric coated tablets, the tablets described in Example 5 are given a thin coat of shellac varnish followed by 20 coats of cellulose acetate phthalate.

EXAMPLE 7

In the preparation of capsules, a mixture of the ingredients described in Example 5 is encapsulated in hard gelatin capsules to give capsules containing 25 mg. of active ingredient. Enteric coating is applied by conventional dipping in cellulose acetate phthalate.

Capsules containing 10 mg. active ingredient are prepared in a similar manner.

EXAMPLE 8

In the preparation of capsules, a mixture of equal parts by weight of 5-methoxy-2-[4-(2-pyrrolidin-1-ylethoxy)anilino]benzothiazole and calcium phosphate is encapsulated in hard gelatin capsules, each capsule containing 25 mg. active ingredient.

Capsules containing 10 mg. active ingredient are prepared in a similar manner.

EXAMPLE 9

In the preparation of enteric coated capsules, the capsules of Example 8 are coated with cellulose acetate phthalate in a conventional manner.

EXAMPLE 10

Suppositories weighing 1 g. and containing 25 mg. of 5-methoxy-2[4-(2-pyrrolidin-1-ylethoxy)anilino]benzothiazole are prepared in a conventional manner using a base consisting of:

| | % w/w |
|---|---|
| polyethylene glycol 4000 | 33 |
| polyethylene glycol 6000 | 47 |
| water | 20 |

Suppositories weighing 1 g. and containing 50 mg. of active ingredient are prepared in a similar manner.

EXAMPLE 11

Compositions analogous to those described in Examples 5 – 10 are prepared using 2-[4-(2-pyrrolidin-1-ylethoxy)anilino]benzothiazole as the active ingredient.

We claim:

1. A therapeutic composition useful for treating depression which comprises an antidepressant effective amount of a benzothiazole compound selected from the group consisting of a compound of the formula

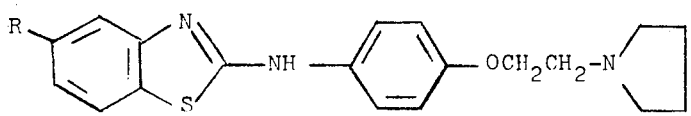

and a pharmaceutically acceptable acid addition salt thereof, wherein R is a member selected from the group consisting of hydrogen and methoxy, together with a pharmaceutically acceptable carrier.

2. A composition according to claim 1 in unit dosage form.

3. A composition according to claim 1 in the form of a tablet or capsule.

4. A composition according to claim 3 containing 10 – 500 mg. of said benzothiazole compound.

5. A composition according to claim 1 in the form of a suppository.

6. A composition according to claim 1 wherein R is methoxy.

7. A composition according to claim 6 wherein said benzothiazole compound is 5-methoxy-2-[4-(2-pyrrolidin-1-ylethoxy)anilino]benzothiazole.

8. A composition according to claim 6 wherein said benzothiazole compound is 2-(4-(2-pyrrolidin-1-ylethoxy)anilino)-benzothiazole.

9. A method of treating depression which comprises administering to a warm-blooded animal an antidepressant effective amount of a benzothiazole compound selected from the group consisting of a compound of the formula

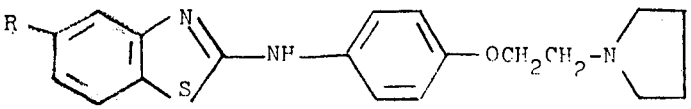

and a pharmaceutically acceptable acid addition salt thereof, wherein R is a member selected from the group consisting of hydrogen and methoxy.

10. A method according to claim 9 wherein R is methoxy.

11. A method according to claim 9 wherein said benzothiazole compound is 5-methoxy-2-[4-(2-pyrrolidin-1-ylethoxy)anilino]-benzothiazole.

12. A method according to claim 9 wherein said benzothiazole compound is administered at a dosage rate of 0.1 – 25 mg./kg./day.

13. A method according to claim 9, wherein said benzothiazole compound is 2-(4-(2-pyrrolidin-1-ylethoxy)anilino-benzothiazole.

* * * * *